United States Patent [19]

Taisha et al.

[11] Patent Number: 4,792,630

[45] Date of Patent: Dec. 20, 1988

[54] PROCESS FOR PREPARING AMINOACETALDEHYDE DIALKYL ACETALS

[75] Inventors: Akira Taisha; Takeo Kawabata, both of Osaka; Takehiko Kakimoto; Kazumasa Hirata, both of Gifu, all of Japan

[73] Assignee: Nippon Gosei Kagaku Kogyo Kabushiki Kaisha, Japan

[21] Appl. No.: 14,666

[22] Filed: Feb. 13, 1987

[30] Foreign Application Priority Data

Feb. 13, 1986 [JP] Japan ................................ 61-30158

[51] Int. Cl.$^4$ .......................................... C07C 85/04
[52] U.S. Cl. ...................................... 564/474; 564/483
[58] Field of Search ............................ 564/474, 483

[56] References Cited

U.S. PATENT DOCUMENTS 4,113,464  9/1978  Stach et al. ........................ 564/474
4,489,011  12/1984  Wang ............................ 260/501.19

FOREIGN PATENT DOCUMENTS 37-823  4/1962  Japan .

Primary Examiner—Glennon H. Hollrah
Assistant Examiner—John A. Sopp
Attorney, Agent, or Firm—McGlew and Tuttle

[57] ABSTRACT

A process for preparing an aminoacetaldehyde dialkyl acetal which comprises reacting a halogenoacetaldehyde dialkyl acetal with ammonia or an alkylamine in an aqueous medium in the simultaneous presence of an alkali metal hydroxide or of an alkaline earth metal hydroxide, and distilling the resulting reaction mixture.

6 Claims, No Drawings

PROCESS FOR PREPARING AMINOACETALDEHYDE DIALKYL ACETALS

BACKGROUND OF THE INVENTION

1. Field of the Invention

The present invention relates to a process for industrially advantageously preparing aminoacetaldehyde dialkyl acetals which are useful as intermediates for medicinals, agricultural chemicals, etc., and also as intermediates for modifiers for high molecular weight compounds such as starch.

2. Description of the Prior Art

Aminoacetaldehyde dialkyl acetals (hereinafter referred to as "aminoacetals") are compounds represented by the following formula:

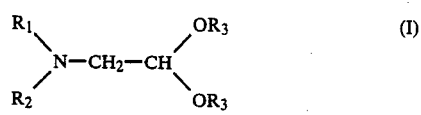

wherein $R_1$ and $R_2$ are each hydrogen or alkyl, and $R_3$ is alkyl.

Typically, it is known to prepare these compounds by reacting a halogenoacetaldehyde dialkyl acetal with an amine, and it is generally reported that this reaction is conducted solely in a non-aqueous system (e.g. Org. Synth. III, 50 (1955); J. Amer. Chem. Soc., 71, 4002 (1949); Ger. Offen. 2,745,588, etc.).

However, the prior art method naturally requires strict selection of the solvent and in turn use of an expensive hazardous alkali substance such as metallic sodium or sodium alcoholate for neutralizing excess amine present in the reaction mixture during work up of the product. Also, in the prior art method, the amine starting material, which is normally a gas, must be used either in the form of a gas per se or as a non-aqueous organic solvent solution, both of which are relatively expensive, as compared to an aqueous solution, which would be very inexpensive. Thus, the known process is economically disadvantageous.

These disadvantages are said to be avoidable when the reaction is conducted in an aqueous system (e.g. Examined Japanese Patent Publication SHO 37-823), which led the present applicants initially to attempt to react methylamine, which is a gas, with chloroacetaldehyde dimethyl acetal in an aqueous system, then to neutralize the resulting reaction mixture, followed by salting out with an alkali for working up the product, and finally to extract the desired compound from the filtrate resulting from the salting out step.

When practiced, however, these latter method steps in an aqueous system were found to involve the separate problem of requiring a large amount of neutralizing alkali during work up and also a very large quantity of extraction solvent since the desired compound, namely, methylaminoacetaldehyde dialkyl acetal, had a very rich solubility in water, i.e. was very soluble in water and was only extractable therefrom with relative difficulty.

The above aqueous system reaction procedure also suffers from other problems. Since the hydrochloric acid, which results from the reaction as a by-product, forms an addition salt with the methylamine, used as starting material, the reaction undesirably consumes 2 moles of methylamine per mole of the other starting material, i.e. chloroacetaldehyde dimethyl acetal. Furthermore, this addition salt which is thereby present in the aqueous reaction system is objectionable in view of the pronounced tendancy thereof to cause corrosion of the reactor, thereby posing an equipment problem as well. Besides, it is impossible to conduct the reaction continuously because there is a need to cool the reaction system at one point in order to recover the excess methylamine remaining in the system after the reaction has been completed.

SUMMARY OF THE INVENTION

It is among the objects of the present invention to overcome the foregoing drawbacks of the prior art, and to provide an efficient and economical process usable on an industrial scale for producing such aminoacetals in high yield.

In this regard, it has been found in accordance with the present invention that all of the foregoing problems can be avoided by reacting a halogenoacetaldehyde dialkyl acetal with ammonia or an alkylamine in an aqueous medium in the simultaneous initial presence of a hydroxide of an alkali metal or of an alkaline earth metal, and distilling the resulting reaction mixture.

According to the present invention, advantageously the hydroxide of alkali metal or alkaline earth metal, which is simultaneously present in the reaction system from the start, i.e. alkali metal hydroxide or alkaline earth metal hydroxide, preferentially reacts with the resulting by-product hydrogen halide, as the latter is continuously produced, so as to form a salt, i.e. the corresponding alkali metal halide or alkaline earth metal halide, and water, such that the hydroxide inherently acts as a scavenging agent for the hydrogen halide, and thus prevents the reaction from causing corrosion of the reactor equipment otherwise resulting from the presence in the system of such hydrogen halide.

The process of the present invention also has another significant related advantage in that only one mole of the ammonia or alkylamine starting material is consumed per mole of the acetal. This is because of the continuous preferential conversion to alkali metal halide or alkaline earth metal halide by the hydroxide of the hydrogen halide as it is produced, which prevents otherwise consumption of such ammonia or alkylamine by undesirable formation of addition salts with the hydrogen halide being continuously generated by the main reaction.

Moreover, the desired product can be favorably and efficiently separated from the aqueous reaction mixture or system by distillation which can be conducted easily on an industrial scale without resorting to the cumbersome procedures heretofore conventionally used, such as salting out and extraction.

DETAILED DESCRIPTION OF THE INVENTION

The "aminoacetals" as referred to herein in accordance with the present invention are represented by the formula (I) above, i.e. $(R_1)(R_2)N-CH_2-CH(OR_3)$ wherein $R_1$ and $R_2$ are each individually hydrogen or alkyl, especially lower alkyl, and are preferably methyl, ethyl or propyl, and each $R_3$ is alkyl, especially lower alkyl, and is preferably methyl, ethyl or propyl.

Examples of such "aminoacetal" product compounds are aminoacetaldehyde dimethyl acetal, aminoacetaldehyde diethyl acetal, aminoacetaldehyde dipropyl acetal, methylaminoacetaldehyde dimethyl acetal, methylaminoacetaldehyde diethyl acetal, methylaminoacetaldehyde dipropryl acetal, ethylaminoacetaldehyde dimethyl acetal, ethylaminoacetaldehyde diethyl acetal, ethylaminoacetaldehyde dipropryl acetal, N,N-dimethylaminoacetaldehyde dimethyl acetal, N,N-dimethylaminoacetaldehyde diethyl acetal, N,N-diethylaminoacetaldehyde dimethyl acetal, N,N-diethylacetaldehyde diethyl acetal, etc.

These aminoacetals are prepared in accordance with the present invention by reacting the corresponding halogenoacetaldehyde dialkyl acetal (e.g. chloroacetaldehyde dimethyl acetal, chloroacetaldehyde diethyl acetal, chloroacetaldehyde dipropryl acetal, bromoacetaldehyde dimethyl acetal, bromoacetaldehyde diethyl acetal, or the like) with ammonia or an alkylamine (e.g. methylamine, ethylamine, dimethylamine, diethylamine, or the like) at an elevated temperature of preferably about 80° to 150° C. This reaction is conducted at an increased or elevated pressure of preferably about 3 to about 20 kg/cm$^2$. It is essential that the reaction be conducted in the presence of a hydroxide of an alkali metal or of an alkaline earth metal. While sodium hydroxide is most useful as the hydroxide, potassium hydroxide, calcium hydroxide, magnesium hydroxide or the like is of course also usable.

The reaction is conducted in an aqueous medium. Preferably, the amine serving as one of the starting materials is used in the form of an aqueous solution, and the alkali metal hydroxide or alkaline earth metal hydroxide is admixed with the other ingredients of the reaction mixture or system also in the form of an aqueous solution, so that the reaction is carried out in an aqueous system.

It will be appreciated that advantageously according to the present invention, the ammonia may be utilized in the form of its hydroxide, i.e. ammonium hydroxide, which inherently is conveniently produced when ammonia is dissolved in aqueous medium to form an aqueous solution of ammonia.

Of course, an aqueous medium can also be positively added to the aqueous system of the above amine and hydroxide solutions without any objection, and a small amount of an organic solvent can be present as well without offsetting the advantages of the present invention.

It is suitable that the reaction be conducted using 4 to 20 moles of ammonia or an alkylamine, 1.0 to 1.5 moles of an alkali metal hydroxide or of an alkaline earth metal hydroxide and 200 to 1,000 ml of an aqueous medium, per mole of the halogenoacetaldehyde dialkyl acetal.

Preferably, the reaction time is 3 to 20 hours.

The reaction mixture obtained is advantageously distilled after the completion of the reaction. Usually, however, any unreacted ammonia or alkylamine still present in the reaction mixture is removed before distillation.

The distillation can be carried out using a distillation column as desired. If the reaction mixture or system is likely to become viscous or muddy with the progress of the distillation, the distillation may be continued with the addition of a suitable amount of water. Water may also, of course, be admixed with the reaction mixture before distillation without any objection.

The desired aminoacetal can be obtained as product efficiently by distillation. Since the acetal forms an azeotropic mixture with water or is close to water in boiling point, the product is obtained usually in the form of a liquid mixture of the aminoacetal and water.

The aminoacetal, even if in the form of a mixture thereof with water, is generally usable free of any difficulty. However, when there is a need to remove the water for a particular use, the mixture may be further purified.

The purification thereof may be effected by any desired method such as extraction, distillation or the like, although it is industrially most useful to remove the water azeotropically in the following manner.

For azeotropic removal of water, at least one organic solvent selected from among aliphatic hydrocarbons, alicyclic hydrocarbons, aromatic hydrocarbons and hydrocarbons halides, and having a boiling point of about 60° to 150° C. is added to the mixture, i.e. the aqueous solution of the acetal.

Examples of such aliphatic hydrocarbons are hexane, heptane, octane, etc. Examples of useful alicyclic hydrocarbons are cyclohexane, methylcyclohexane, ethylcyclohexane, etc. Examples of useful aromatic hydrocarbons are toluene, benzene, xylene, ethylbenzene, chlorobenzene, etc. Examples of useful hydrocarbon halides are dichloromethane, chloroform, carbon tetrachloride, 1,2-dichloroethane, trichloroethylene, etc. Various isomers or substituted compounds of these organic solvents are of course usable insofar as they are about 60° to 150° C. in boiling point.

Among these organic solvents usable for the azeotropic removal of water, most desirable to use are heptane as as aliphatic hydrocarbon, cyclohexane as an alicyclic hydrocarbon, toluene and benzene as aromatic hydrocarbons, and 1,2-dichloroethane as a hydrocarbon halide, i.e. from the overall viewpoint of availability and facility of separation from water.

The water can be azeotropically removed from the aqueous solution of amino acetal by adding the organic solvent to the solution at one time or in divided portions and refluxing the resulting mixture with heating, without resorting to any special procedure. When required, the reflux is conducted with stirring. The distillate is substantially free from the aminoacetal and composed of water and the organic solvent. The organic solvent after being separated from the water is advantageously returned to the system again. Although the amount of the organic solvent to be used is not limited specifically, it is generally equal to or greater than the amount by weight of the aminoacetal contained in the aqueous solution. When the distillate becomes almost free from water, the purifying procedure is terminated. In this way, the water is almost completely removed from the aqueous solution of aminoacetal, giving the desired aminoacetaldehyde dialkyl acetal dissolved in the organic solvent.

When required, the organic solvent is of course removed from the solution, so as to provide the desired aminoacetal with a high purity.

Thus, the process of the present invention produces aminoacetals very economically through efficient use of apparatus and is therefore of immense industrial usefulness.

The process of the present invention is described in greater detail with reference to the following examples, which are set forth by way of illustration and not limitation.

EXAMPLE 1

One mole (124.5 g) of chloroacetaldehyde dimethyl acetal (mol. wt. 124.5), 465.0 g of 40% aqueous solution of methylamine and 40.4 g of sodium hydroxide were placed into an autoclave, then heated and initiated to reaction at a gauge pressure of 4.0 kg/cm². The reaction was continued under the conditions of 4.0 to 7.0 kg/cm² and 86° to 113° C. After the completion of the reaction, the unreacted methylamine (151.8 g) was recovered by purging. Subsequently, the reaction mixture was distilled, giving 340 g of an aqueous solution of methylaminoacetaldehyde dimethyl acetal (mol. wt. 119). When analyzed by gas chromatography, the solution was found to contain 110 g of the acetal (yield 92.4%).

EXAMPLE 2

The same procedure as in Example 1 was repeated with the exception of using 1214 g of 28% ammonium hydroxide in place of methylamine and conducting the reaction at a temperature of 98° to 116° C. at a pressure of 7.0 to 9.0 kg/cm² for 15 hours, whereby 7940 g of an aqueous solution of aminoacetaldehyde dimethyl acetal (mol. wt. 105) was obtained which contained 101.2 g of the acetal (yield 96.4%).

EXAMPLE 3

The same procedure as in Example 1 was repeated with the exception of using chloroacetaldehyde diethyl acetal (mol. wt. 152.5) in place of chloroacetaldehyde dimethyl acetal and conducting the reaction at a temperature of 85° to 120° C. and at a pressure of 4.0 to 8.0 kg/cm² for 10 hours. The reaction gave 413.6 g of an aqueous solution of methylaminoacetaldehyde diethyl acetal (mol. wt. 147) which contained 90.1 g of the acetal (yield 61.3%).

EXAMPLES 4 AND 5

The same procedure as in Example 1 was repeated except that potassium hydroxide and calcium hydroxide, respectively, was used in place of sodium hydroxide.

Example 4 afforded 353 g of an aqueous solution of methylaminoacetaldehyde dimethyl acetal (yield of the acetal 89.8%). Example 5 gave 336 g of the same aqueous solution (yield of the acetal 90.3%).

EXAMPLE 6

The same procedure as in Example 2 was repeated except that chloroacetaldehyde diethyl acetal was reacted with ammonium hydroxide, giving 867 g of an aqueous solution of aminoacetaldehyde diethyl acetal (yield of the acetal 56.2%).

EXAMPLE 7

In the same manner as in Example 1, 590.0 g of an aqueous solution of methylaminoacetaldehyde dimethyl acetal (content of the acetal 200 g) was prepared.

With addition of 200 g of toluene (boiling point 110° C.), the solution was refluxed in a still with heating at 85° to 120° C.

The mixture soon started to release a distillate (at the internal temperature of the still of 92° C.). Water was removed from the distillate, and the toluene separated off was returned to the still. This procedure was repeated suitably for about 5 hours for the azeotropic removal of water until the distillate no longer separated into two layers. The internal temperature was 120° C. when the procedure was terminated.

The resulting liquid containing the acetal was subjected to gas chromatography to determine the contents of the acetal and the remaining water. The liquid was found to be a toluene solution containing about 198 g of the acetal (content 99.2%) and about 0.3 g of water (content 0.1%). Thus, the water was almost completely removed.

The water was also removed from the same aqueous acetal solution as above in the same manner as above in additional instances except that toluene was correspondingly replaced by heptane (boiling pint 98° C.), cyclohexane (boiling point 81° C.) or 1,2-dichloroethane (boiling point 83.7° C.), as the case may be.

The corresponding liquids obtained by the removal of water were checked for the acetal and remaining water ratios. The results are listed in the table below.

EXAMPLES 8 TO 10

The same azeotropic water removal procedure as in Example 7 was repeated using various organic solvents except that the aqueous solution of methylaminoacetaldehyde dimethyl acetal was correspondingly replaced by an aqueous solution of aminoacetaldehyde dimethyl acetal Example 8), methylaminoacetaldehyde diethyl acetal (Example 9) or aminoacetaldehyde diethyl acetal (Example 10), as the case may be.

The corresponding liquids obtained by the removal of water were checked for the acetal and remaining water ratios. The results are also listed in the table below.

TABLE

| Org. solvent | Ex. 7 | Ex. 8 | Ex. 9 | Ex. 10 |
| --- | --- | --- | --- | --- |
| Toluene | 99.2 (%) | 99.1 (%) | 99.0 (%) | 98.9 (%) |
|  | 0.1 | 0.2 | 0.1 | 0.2 |
| Heptane | 99.0 | 98.7 | 99.0 | 98.5 |
|  | 0.3 | 0.4 | 0.3 | 0.3 |
| Cyclohexane | 99.0 | 98.9 | 99.1 | 99.1 |
|  | 0.3 | 0.3 | 0.3 | 0.3 |
| Benzene | 99.1 | 99.0 | 99.2 | 98.8 |
|  | 0.3 | 0.4 | 0.2 | 0.4 |
| 1,2-Dichloroethane | 98.9 | 98.8 | 98.8 | 98.5 |
|  | 0.5 | 0.5 | 0.4 | 0.4 |

Note: The upper or first value for each solvent was the content of the aminoacetal concerned, and the lower or second value was the content of attendant water.

ADVANTAGES

The process of the present invention causes no corrosion to the system apparatus, diminishes the consumption of alkylamines, affords the desired product by the simple procedure of distillation and is therefore exceedingly superior to the conventional process.

It will be realized that the foregoing specification and accompanying examples are set forth by way of illustration and not limitation, and that various modifications and changes may be made therein without departing from the spirit and scope of the present invention, which is to be limited solely by the scope of the appended claims.

What is claimed is:

1. Process for preparing an aminoacetaldehyde dialkyl acetal, which comprises
   reacting a halogenoacetaldehyde dialkyl acetal with ammonia or an alkylamine in an aqueous medium in the simultaneous presence, from the start of the reaction, of a hydroxide of an alkali metal or of an alkaline earth metal, distilling the resulting reaction mixture to recover the thereby produced aminoacetaldehyde dialkyl acetal in the form of an aqueous solution as distilled product, and purifying the recovered distilled product acetal aqueous solution by adding thereto an organic solvent having a boiling point of about 60° to 150° C. and selected from the group consisting of aliphatic hydrocarbons, alicyclic hydrocarbons, aromatic hydrocarbons and hydrocarbon halides, as azeotropic removal solvent, and azeotropically removing the attendant water from the resulting mixture in the presence of said azeotropic removal solvent to provide such purified acetal product substantially free of attendant water and of such removal solvent.

2. Process of claim 1 wherein the water is removed sufficiently to provide a purified product containing at most about 0.4 to 0.5% water.

3. Process of claim 1 wherein the hydroxide is sodium hydroxide.

4. Process of claim 1 wherein 4 to 20 moles of ammonia or an alkylamine, 1.0 to 1.5 moles of the hydroxide and 200 to 1,000 ml of the aqueous medium are used per mole of the halogenoacetaldehyde dialkyl acetal.

5. Process of claim 1 wherein the reaction is carried out at elevated temperture under elevated pressure.

6. Process of claim 1 wherein the reaction is carried out at about 80° to 150° C. and a pressure of about 3 to 20 kg/cm$^2$.

* * * * *